(12) United States Patent
Nakagawa et al.

(10) Patent No.: US 11,937,960 B2
(45) Date of Patent: Mar. 26, 2024

(54) MEDICAL IMAGE DIAGNOSIS APPARATUS

(71) Applicant: CANON MEDICAL SYSTEMS CORPORATION, Otawara (JP)

(72) Inventors: Shouichi Nakagawa, Otawara (JP); Keita Yonemori, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 152 days.

(21) Appl. No.: 17/387,133

(22) Filed: Jul. 28, 2021

(65) Prior Publication Data
US 2022/0031269 A1   Feb. 3, 2022

(30) Foreign Application Priority Data
Jul. 31, 2020   (JP) .................. 2020-130320

(51) Int. Cl.
*A61B 6/03* (2006.01)
*A61B 6/00* (2006.01)

(52) U.S. Cl.
CPC .............. *A61B 6/4435* (2013.01); *A61B 6/03* (2013.01); *A61B 6/032* (2013.01)

(58) Field of Classification Search
CPC .......... A61B 6/4435; A61B 6/03; A61B 6/032
See application file for complete search history.

(56) References Cited

U.S. PATENT DOCUMENTS

| | | | | |
|---|---|---|---|---|
| 6,735,274 B1 * | 5/2004 | Zahavi | ................. | A61B 6/4028 378/4 |
| 2006/0018437 A1 * | 1/2006 | Russinger | .............. | A61B 6/035 378/197 |
| 2008/0192885 A1 * | 8/2008 | Teofilovic | ............ | G01N 23/046 378/4 |
| 2017/0135657 A1 * | 5/2017 | Bichler | ................. | A61B 6/035 |

FOREIGN PATENT DOCUMENTS

| | | |
|---|---|---|
| JP | 06-38960 A | 2/1994 |
| JP | 2007-130119 A | 5/2007 |
| JP | 2015-198769 A | 11/2015 |
| JP | 2016-209724 A | 12/2016 |
| JP | 2017-077464 A | 4/2017 |

OTHER PUBLICATIONS

Japanese Office Action dated Jan. 16, 2024, in Japanese Patent Application No. 2020-130320, 2 pages.

* cited by examiner

*Primary Examiner* — David P Porta
*Assistant Examiner* — Shun Lee
(74) *Attorney, Agent, or Firm* — Oblon, McClelland, Maier & Neustadt, L.L.P.

(57) ABSTRACT

A medical image diagnosis apparatus according to an embodiment includes: a first supporting part, a second supporting part, and one or more columns. The first supporting part is configured to support an imaging system related to imaging a subject to be examined. The second supporting part is configured to support the first supporting (Continued)

part from underneath the first supporting part. The one or more columns are configured to support the second supporting part so as to be movable along a vertical direction.

8 Claims, 6 Drawing Sheets

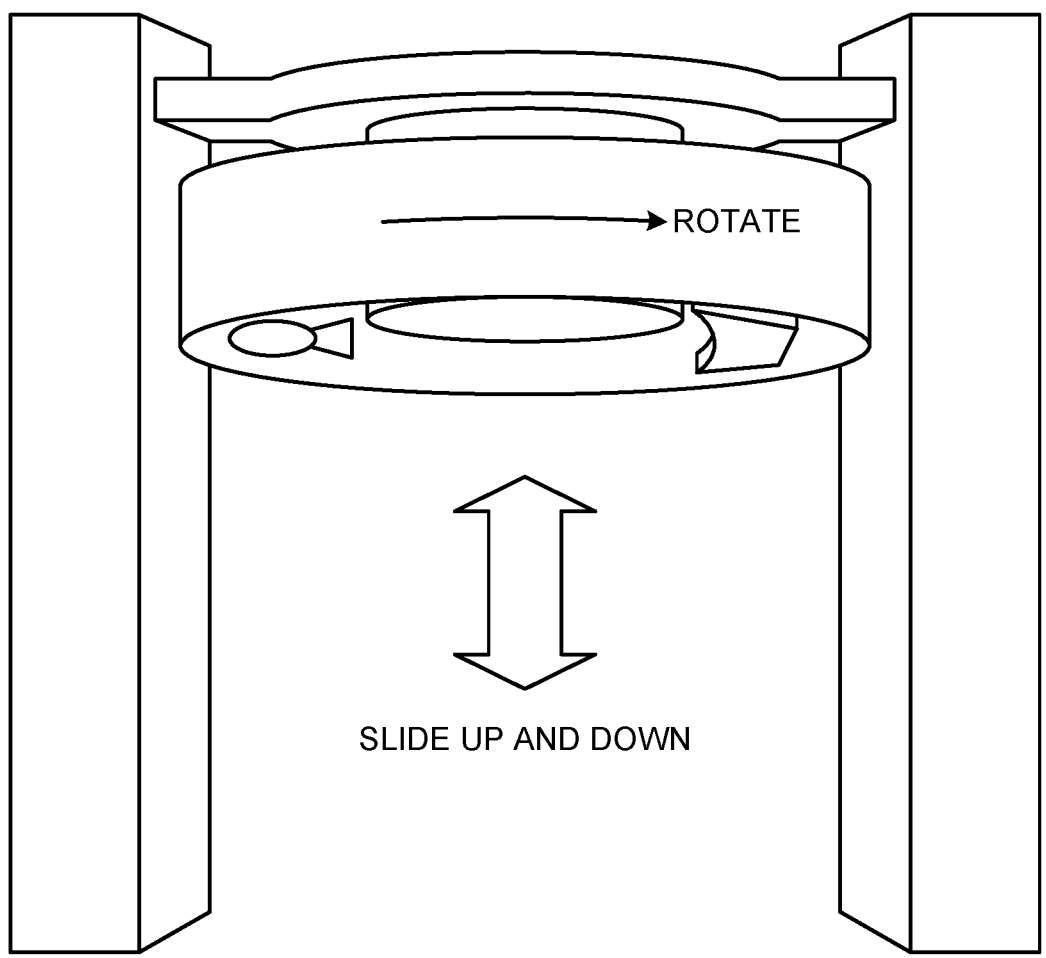

MEDICAL IMAGE DIAGNOSIS APPARATUS

CROSS-REFERENCE TO RELATED APPLICATIONS

This application is based upon and claims the benefit of priority from Japanese Patent Application No. 2020-130320, filed on Jul. 31, 2020; the entire contents of which are incorporated herein by reference.

FIELD

Embodiments described herein relate generally to a medical image diagnosis apparatus.

BACKGROUND

Conventionally-known medical image diagnosis apparatuses such as X-ray Computed Tomography (CT) apparatuses include those that are capable of imaging a subject to be examined in a standing state or a sitting state. In such apparatuses, generally speaking, a rotating frame configured to support an imaging system such as an X-ray tube and an X-ray detector is attached while hanging from a supporting frame. In this type of configuration, the rotating frame tends to be heavy in order to ensure the strength to support the imaging system.

BRIEF DESCRIPTION OF THE DRAWINGS

FIG. 9 is a diagram illustrating an example of a standing CT apparatus according to a comparison example.

DETAILED DESCRIPTION

Exemplary embodiments of a medical image diagnosis apparatus will be explained in detail below with reference to the accompanying drawings.

First Embodiment

A medical image diagnosis apparatus according to an embodiment includes: a first supporting part, a second supporting part, and one or more columns. The first supporting part is configured to support an imaging system related to imaging a subject to be examined. The second supporting part is configured to support the first supporting part from underneath the first supporting part. The one or more columns are configured to support the second supporting part so as to be movable along a vertical direction.

Figure 1:
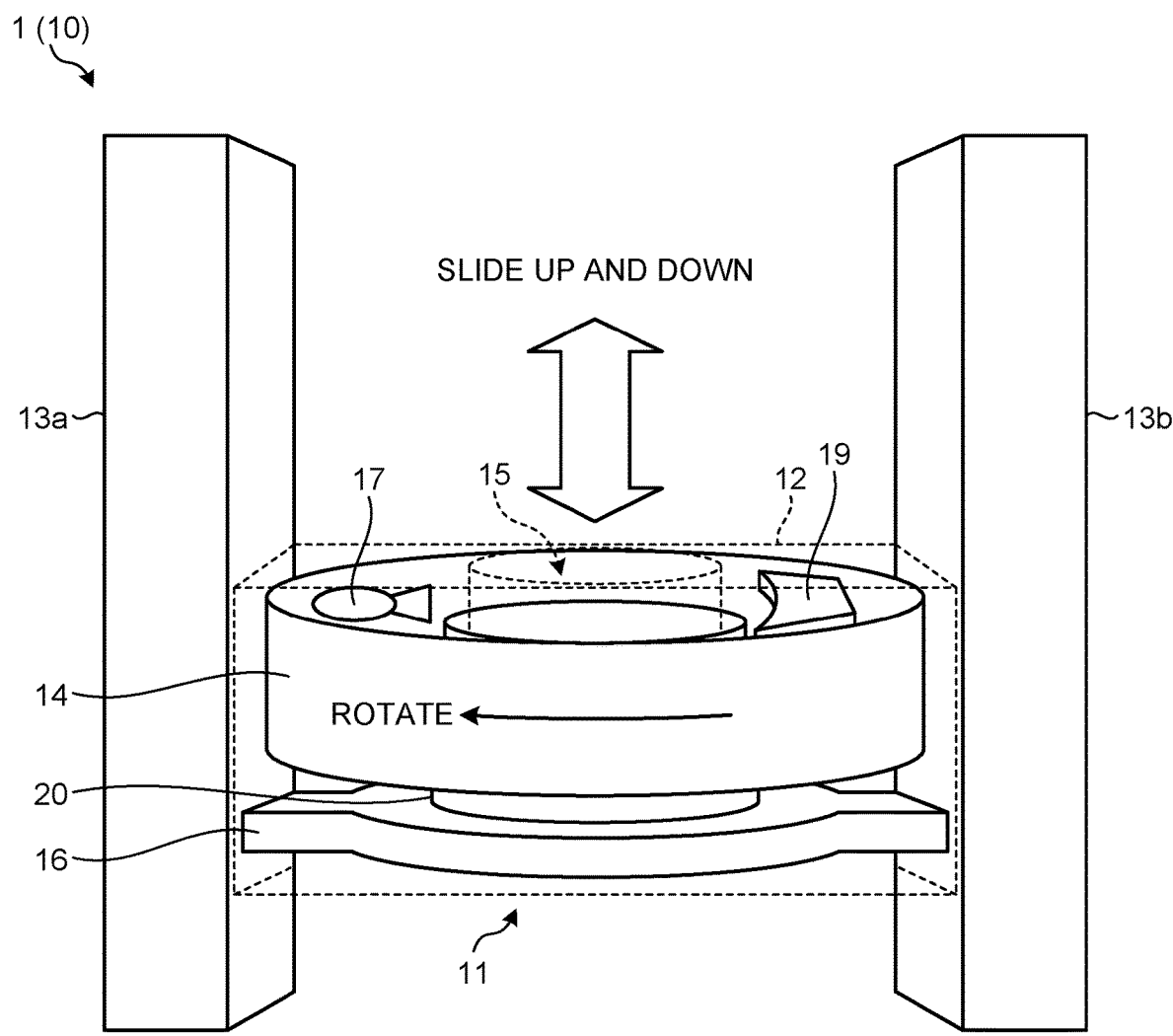
FIG. 1 is a drawing illustrating an example of the appearance of a gantry device included in a standing CT apparatus according to a first embodiment.

FIG. 1 is a drawing illustrating an example of the appearance of a gantry device 10 included in a standing Computed Tomography (CT) apparatus 1 according to the present embodiment. The standing CT apparatus 1 is an X-ray CT apparatus capable of imaging a subject to be examined in a standing state or a sitting state and serves as an example of the medical image diagnosis apparatus according to the present embodiment. Instead of the entirety of the standing CT apparatus 1, the gantry device 10 may be used as an example of the medical image diagnosis apparatus according to the present embodiment. The subject in the present embodiment is a patient, for example.

The standing state denotes a state in which the subject (hereinafter, "patient") is standing on the floor surface on which the standing CT apparatus 1 is installed. The sitting state denotes a state in which the patient is sitting on a wheelchair or a chair (hereinafter, "wheelchair or the like"). It is sufficient when the standing CT apparatus 1 is capable of imaging a patient at least in the standing state.

As illustrated in FIG. 1, the gantry device 10 of the standing CT apparatus 1 includes a gantry cover 12, columns 13a and 13b, a rotating frame 14, a supporting frame 16, an X-ray tube 17, and an X-ray detector 19.

The X-ray tube 17 and the X-ray detector 19 are included in the imaging system related to imaging the patient according to the present embodiment. In addition, the imaging system may further include a data acquiring circuit, a high-voltage generator, a collimator, a wedge, and the like (not illustrated). Further, the imaging system, the gantry cover 12, the rotating frame 14, and the supporting frame 16 will collectively be referred to as a gantry 11. The gantry 11 is configured to move in vertical directions along the columns 13a and 13b.

The rotating frame 14 is configured to support the imaging system including at least the X-ray tube 17 and the X-ray detector 19. For example, the rotating frame 14 includes an annular-shaped bottom face having a circular through hole at the center thereof; an outer wall surrounding the bottom face along the outer circumference of the bottom face; and an inner wall surrounding the through hole. Further, for example, the rotating frame 14 is a cast product formed by using metal such as aluminum. Details of the shape of the rotating frame 14 will be explained later. The rotating frame 14 is an example of the first supporting part according to the present embodiment. In the present embodiment, being circular includes being oval.

As illustrated in FIG. 1, the supporting frame 16 is positioned lower than the rotating frame 14 is. The supporting frame 16 is configured to support the rotating frame 14 from underneath the rotating frame 14.

Further, as illustrated in FIG. 1, the supporting frame 16 has a circular through hole at the center thereof. For example, in a connecting part 20 between the supporting frame 16 and the rotating frame 14, a bearing is provided so that the supporting frame 16 rotatably supports the rotating frame 14. For example, the bearing is provided along the outer circumferences of the through hole formed in the supporting frame 16 and the through hole formed in the rotating frame 14. The supporting frame 16 is an example of the second supporting part according to the present embodiment. For example, the supporting frame 16 is formed by using metal such as aluminum. Further, the supporting frame 16 is supported by the columns 13a and 13b.

The columns 13a and 13b are configured to support the supporting frame 16 so as to be movable along the vertical directions. In the following sections, when not being particularly distinguished from each other, the columns 13a and 13b will be referred to as the columns 13.

Typically, the columns 13 are provided in two lateral parts of the gantry 11. To have an X-ray CT imaging process performed on the patient having a sitting or standing posture, the columns 13 are configured to support the gantry 11 so as to be slidable perpendicularly to the floor surface, while the gantry 11 is oriented so that the central axis (indicated in FIG. 2) of a bore 15 is substantially perpendicular to the floor surface. For example, the columns 13 are provided with a rail extending along the vertical direction, so that the supporting frame 16 is able to move on the rail in the vertical directions.

It is sufficient when the gantry device 10 includes at least one column 13, and the quantity of the columns 13 does not necessarily have to be two. For example, a single column 13 may be connected to only one of the two lateral parts of the gantry 11. Further, although the one or more columns 13 may commonly have a columnar shape such as a circular cylindrical shape or a prismatic shape, the one or more columns 13 may each have any shape as long as it is possible to support at least one of the lateral parts of the gantry 11.

The gantry cover 12 is configured to cover the rotating frame 14 and the supporting frame 16. As illustrated in FIG. 1, similarly to the rotating frame 14, the gantry cover 12 is a structure in the shape of a substantially circular cylinder that has a circular through hole formed at the center thereof and an inner wall surrounding the through hole. The shape of the gantry cover 12 illustrated in FIG. 1 is merely an example, and possible embodiments are not limited to this example. The gantry cover 12 is an example of the cover according to the present embodiment.

The space having a substantially circular cylindrical shape and being surrounded by the inner wall of the gantry cover 12 is referred to as the bore 15. When an imaging process is performed by the standing CT apparatus 1, the patient in a standing or sitting state is positioned inside the bore 15.

Next, the configuration of the standing CT apparatus 1 will be explained further in detail, with reference to FIG. 2.

Figure 2:
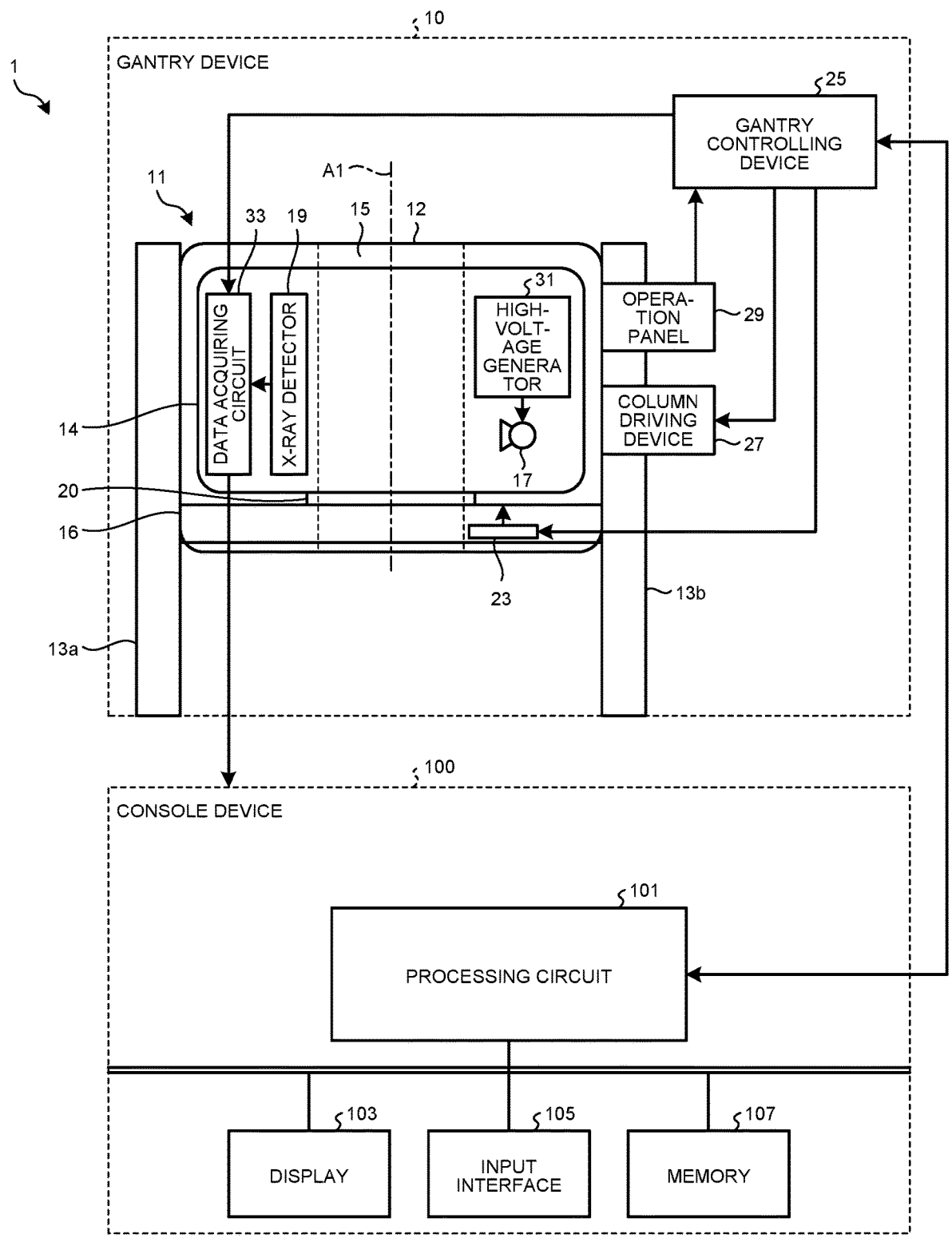
FIG. 2 is a block diagram illustrating an exemplary configuration of the standing CT apparatus according to the first embodiment.

FIG. 2 is a block diagram illustrating an exemplary configuration of the standing CT apparatus 1 according to the present embodiment. As illustrated in FIG. 2, the standing CT apparatus 1 according to the present embodiment includes the gantry device 10 and a console device 100. For example, the gantry device 10 is installed in a CT examination room, whereas the console device 100 is installed in a control room adjacent to the CT examination room.

The gantry device 10 and the console device 100 are connected in a wired or wireless manner so as to be able to communicate with each other. The gantry device 10 is a scan device having a configuration to perform the X-ray CT imaging process on the patient having a sitting or standing posture. The console device 100 is a computer configured to control the gantry device 10.

Further, as constituent elements of the gantry device 10, FIG. 2 illustrates a rotation driving device 23, a gantry controlling device 25, a column driving device 27, an operation panel 29, a high-voltage generator 31, and a data acquiring circuit 33, in addition to the constituent elements illustrated in FIG. 1.

Under control of the console device 100, the gantry controlling device 25 is configured to output a drive signal to the rotation driving device 23. The gantry controlling device 25 may be called a gantry controlling circuit.

According to control exercised by the gantry controlling device 25, the rotation driving device 23 is configured to generate motive power to rotate the rotating frame 14. In one example, the rotation driving device 23 generates the motive power by realizing the driving at a rotation speed corresponding to a duty cycle or the like of the drive signal from the gantry controlling device 25. For example, the rotation driving device 23 is realized by using a motor such as a direct drive motor or a servo motor. For example, the rotation driving device 23 is housed in the gantry cover 12.

The rotating frame 14 is configured to rotate on a central axis A1 of the bore 15 at a constant angular speed, by receiving the motive power from the rotation driving device 23.

According to the control exercised by the gantry controlling device 25, the column driving device 27 is configured to generate motive power to slide the gantry 11 in vertical directions. In one example, the column driving device 27 generates the motive power by realizing the driving at a rotation speed corresponding to a duty cycle or the like of a drive signal from the gantry controlling device 25. By receiving the motive power from the column driving device 27, the columns 13 cause the gantry 11 to slide with respect to the vertical directions. For example, the column driving device 27 may be realized by using a motor such as a servo motor. The column driving device 27 is housed in the columns 13.

The operation panel 29 is realized by using a switch button, a touchpad on which input operations can be performed by touching an operation surface thereof, a touch panel display in which a display screen and a touchpad are integrally formed, and/or the like. The operation panel 29 is configured to convert input operations received from an operator into electrical signals and to output the electrical signals to the gantry controlling device 25. For example, the operation panel 29 is configured to receive a selecting operation to select from between: a sitting imaging mode in which the patient is imaged while in a sitting state; and a standing imaging mode in which the patient is imaged while in a standing state.

The high-voltage generator 31 is fixed to the rotating frame 14, for example. Under control of the gantry controlling device 25, the high-voltage generator 31 is configured to generate high voltage to be applied to the X-ray tube 17, from electric power supplied thereto from a power source device (not illustrated) of the gantry 11 via an annular electrode. The high-voltage generator 31 and the X-ray tube 17 are connected to each other via a high-voltage cable (not illustrated), so that the high voltage generated by the high-voltage generator 31 is applied to the X-ray tube 17 via the high-voltage cable.

The X-ray tube 17 is configured to generate X-rays by receiving the high voltage applied from the high-voltage generator 31. The X-rays generated by the X-ray tube 17 pass through a wedge (not illustrated) serving as a filter used for adjusting the amount of X-rays. Further, the radiation range of the X-rays that have passed through the wedge is narrowed down by a collimator (not illustrated).

The data acquiring circuit 33 is connected to the X-ray detector 19 on the inside of the gantry 11 and is configured to acquire, with respect to each view, digital data indicating the intensity of X-rays attenuated by the patient. The data acquiring circuit 33 is realized, for example, by using a semiconductor integrated circuit in which an integrating circuit provided with respect to each of a plurality of X-ray detecting elements and an Analog/Digital (A/D) converter are installed in parallel to each other. The integrating circuit is configured to generate an integral signal by integrating electrical signals from the X-ray detecting elements over a prescribed view period.

The A/D converter included in the data acquiring circuit 33 is configured to generate digital data having a data value corresponding to a peak value of the integral signal by performing an A/D conversion on the generated integral signal. The digital data resulting from the conversion is called raw data. The raw data is a set of digital values indicating X-ray intensities and each being identified with a channel number and a row number of the X-ray detecting element by which the data was generated and with a view number indicating the acquired view. For example, the raw data is supplied to the console device 100 via a contactless data transfer device (not illustrated) housed in the gantry 11. The data acquiring circuit 33 may be referred to as a Data Acquisition System (DAS).

By following a command from the console device 100, the gantry controlling device 25 is configured to control the high-voltage generator 31, the rotation driving device 23, the column driving device 27, and the data acquiring circuit 33. As a hardware resource, the gantry controlling device 25 includes a processing device (a processor) and one or more storage devices (memory elements) such as a Read-Only Memory (ROM), a Random Access Memory (RAM), and/or the like. The processing device realizes the abovementioned functions by reading and realizing programs saved in a storage device. Instead of saving the programs in the storage device, it is also acceptable to directly incorporate the programs in the circuit of the processing device. In that situation, the processing device realizes the abovementioned functions by reading and executing the programs incorporated in the circuit thereof.

Next, the console device 100 will be explained. As illustrated in FIG. 2, the console device 100 includes a processing circuit 101, a display 103, an input interface 105, and a memory 107. Data communication among the processing circuit 101, the display 103, the input interface 105, and the memory 107 is performed via a bus.

The processing circuit 101 is configured to control operations of the entirety of the standing CT apparatus 1. For example, in the standing CT apparatus 1, various types of processing functions are stored in the memory 107 in the form of computer-executable programs. The processing circuit 101 is a processor configured to realize the functions corresponding to the programs, by reading and executing the programs from the memory 107.

For example, the processing circuit 101 is configured to perform a CT scan, by controlling the gantry device 10 on the basis of an input operation received from the operator via the input interface 105. Further, by controlling the data acquiring circuit 33, the processing circuit 101 is configured to control a projection data acquiring process performed by the gantry device 10. Further, the processing circuit 101 is configured to generate data by performing pre-processing processes such as a logarithmic conversion process, an offset correcting process, an inter-channel sensitivity correcting process, a beam hardening correction, and/or the like, on the raw data output from the data acquiring circuit 33. Further, the processing circuit 101 is configured to generate CT image data by performing a reconstructing process that uses a filtered back projection method, a successive approximation reconstruction method, or the like, on the data resulting from the pre-processing processes. Further, on the basis of an input operation received from the operator via the input interface 105, the processing circuit 101 is configured to convert the CT image data into a tomographic image data on an arbitrary cross-sectional plane or three-dimensional image data. The processing circuit 101 is configured to cause the display 103 to display a generated CT image or any of various types of other images.

For example, the memory 107 is realized by using a semiconductor memory element such as a Random Access Memory (RAM) or a flash memory, or a hard disk, an optical disk, or the like. For example, the memory 107 is configured to store therein projection data and CT image data. Further, for example, the memory 107 is configured to store therein programs used by circuits included in the standing CT apparatus 1 for realizing functions thereof. Alternatively, the memory 107 may be realized with a group of servers (a cloud) connected to the standing CT apparatus 1 via a network.

The display 103 is configured to display various types of information. For example, the display 103 displays various types of images such as the CT image generated by the processing circuit 101 and a display image. Further, the display 103 may display a Graphical User Interface (GUI) used for receiving various types of operations from the operator. For example, the display 103 may be a liquid crystal display, a Cathode Ray Tube (CRT) display, an organic Electroluminescence (EL) display, a Light Emitting Diode (LED) display, a plasma display, or any of other arbitrary displays known in the relevant technical field. The display 103 may be of a desktop type or may be configured by using a tablet terminal or the like capable of wirelessly communicating with the main body of the console device 100. Further, the display 103 may be provided for the gantry device 10.

The input interface 105 is configured to receive various types of input operations from the operator, to convert the received input operations into electrical signals, and to output the electrical signals to the processing circuit 101. For example, the input interface 105 receives, from the operator, operations to input a reconstruction condition used at the time of reconstructing the CT image data, an image processing condition used at the time of generating a post-processing image from the CT image data, and the like.

For example, the input interface 105 is realized by using a trackball, a switch button, a mouse, a keyboard, a touchpad on which input operations can be performed by touching an operation surface thereof, a touch screen in which a display screen and a touchpad are integrally formed, a contactless input circuit using an optical sensor, an audio input circuit, and/or the like. When the display 103 is a touch screen, the display 103 and the input interface 105 may be integrated together. Further, the input interface is connected to the processing circuit 101 and is configured to convert input operations received from the operator into electrical signals and to output the electrical signals to the processing circuit 101. In the present disclosure, the input interface does not necessarily have to include one or more physical operation component parts such as a mouse, a keyboard, and/or the like. For instance, possible examples of the input interface include an electrical signal processing circuit configured to receive an electrical signal corresponding to an input operation from an external input device provided separately from the device and to output the electrical signal to the processing circuit 101.

Further, the input interface 105 may be provided for the gantry device 10. Further, the input interface 105 may be configured by using a tablet terminal or the like capable of wirelessly communicating with the main body of the console device 100.

Possible configurations of the gantry controlling device 25 and the processing circuit 101 described above are not limited to the example in which each of the "processors" reads and executes the programs corresponding to the functions from the storage circuit. Further, in the present embodiments, the term "processor" denotes, for example, a Central Processing Unit (CPU), a Micro Processing Unit (MPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). When the processor is a CPU, for example, the processor realizes the functions by reading and executing the programs saved in a storage circuit. In contrast, when the processor is an ASIC, instead of saving the programs in the storage circuit, the functions are directly incorporated in the circuit of the processor as a logic circuit. The processors of the present embodiment do not each necessarily have to be structured as a single circuit. It is also acceptable to structure one processor by combining together a plurality of independent circuits, so as to realize the functions thereof. Further, it is also possible to integrate two or more constituent elements into one processor so as to realize the functions thereof.

Figure 3:
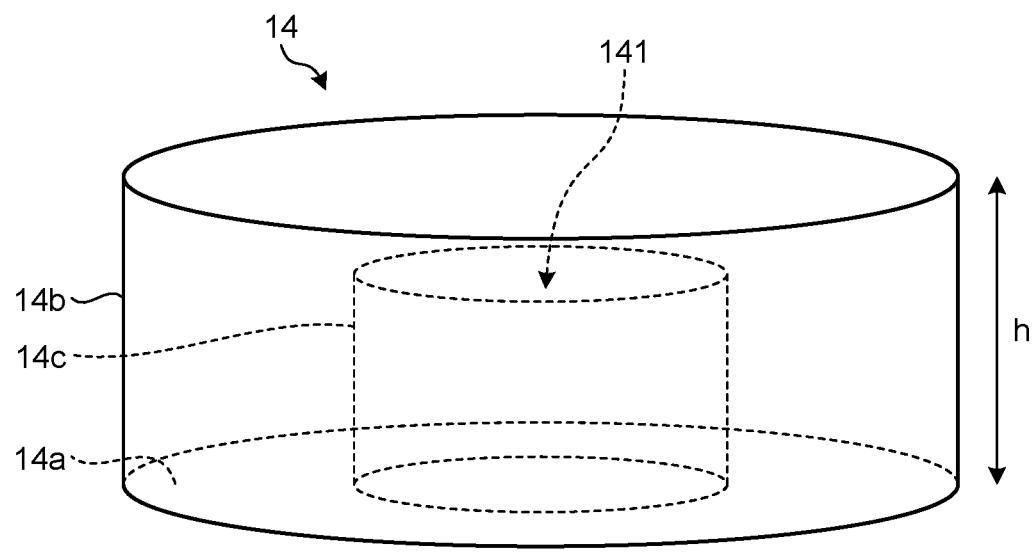
FIG. 3 is a drawing illustrating an example of the appearance of a rotating frame according to the first embodiment.

Next, the shape of the rotating frame 14 according to the present embodiment will be explained further in detail. FIG. 3 is a drawing illustrating an example of the appearance of the rotating frame 14 according to the present embodiment. In FIG. 3, the configuration of the connecting part 20 and the configuration of the imaging system provided in the rotating frame 14 are omitted from the drawing.

As illustrated in FIG. 3, the rotating frame 14 according to the present embodiment includes: an annular-shaped bottom face 14a having a circular through hole 141 formed at the center thereof; an outer wall 14b surrounding the bottom face 14a along the outer circumference of the bottom face 14a; and an inner wall 14c surrounding the through hole 141.

Further, the rotating frame 14 in the present embodiment is in an open state because no lid is provided as a top face. Because the upper part of the rotating frame 14 is covered by the gantry cover 12, the imaging system is not exposed even though the rotating frame 14 itself has no lid. Alternatively, the rotating frame 14 may have a lid that can be opened and closed.

The bottom face 14a of the rotating frame 14 is configured to support the imaging system. More specifically, the imaging system including the X-ray tube 17 and the X-ray detector 19 is fixed onto the bottom face 14a of the rotating frame 14.

Further, the outer wall 14b is an example of the lateral wall according to the present embodiment. The height h of the outer wall 14b of the rotating frame 14 in the present embodiment is equal to or taller than the height of the imaging system. For example, the height h of the outer wall 14b is equal to or taller than the heights of at least the X-ray tube 17 and the X-ray detector 19.

Further, as illustrated in FIG. 3, the height of the inner wall 14c is shorter than the height h of the outer wall 14b. Alternatively, it is also acceptable to configure the rotating frame 14 so as not to have the inner wall 14c.

As described above, the standing CT apparatus 1 according to the present embodiment includes the rotating frame 14 configured to support the imaging system, the supporting frame 16 configured to support the rotating frame 14 from underneath the rotating frame 14; and at least one column 13 configured to support the supporting frame 16 so as to be movable along the vertical directions. As a result, in the standing CT apparatus 1 according to the present embodiment, there is a lower risk that the imaging system may fall off from the rotating frame 14 than in the situation where the rotating frame 14 is attached while hanging from the supporting frame 16. Accordingly, the strength required of the rotating frame 14 is lower than in the situation where the rotating frame 14 is attached while hanging from the supporting frame 16. Consequently, according to the present embodiment, it is possible to make the rotating frame 14 lighter in weight. Further, because the rotating frame 14 is lighter, it is possible to make the total weight of the standing CT apparatus 1 lighter.

Further, in the standing CT apparatus 1 according to the present embodiment, the imaging system includes at least the X-ray tube 17 and the X-ray detector 19, while the supporting frame 16 is configured to rotatably support the rotating frame 14. Although the rotation of the rotating frame 14 imposes a load on the connecting part 20 positioned between the rotating frame 14 and the supporting frame 16, because the standing CT apparatus 1 according to the present embodiment is configured so that the supporting frame 16 supports the rotating frame 14 from underneath, it is possible to reduce the load.

Further, in the standing CT apparatus 1 according to the present embodiment, the rotating frame 14 includes the bottom face 14a configured to support the imaging system and the outer wall 14b provided along the outer circumference of the rotating frame 14. In the standing CT apparatus 1 according to the present embodiment, because the bottom face 14a is configured to support the imaging system, it is possible to reduce the load imposed on the rotating frame 14 to have the imaging system supported, compared to the situation where the imaging system is hung from the top face of the rotating frame 14.

FIG. 9 is a diagram illustrating an example of a standing CT apparatus according to a comparison example. In FIG. 9, the gantry cover is omitted from the drawing.

Generally speaking, in standing CT apparatuses adopting a configuration of a CT apparatus used for recumbent-posture imaging or the like, a rotating frame configured to support an imaging system is attached while hanging from a supporting frame, as illustrated in the comparison example in FIG. 9. In this configuration, the connecting part 20 between the rotating frame and the supporting frame is required to have a high strength. Further, in the comparison example, because the imaging system is installed so as to hang from the rotating frame, the weight of the rotating frame tends to be heavy to ensure the strength to support the imaging system.

As explained above, as for the standing CT apparatus 1 according to the present embodiment, it is possible to make the total weight of the entire standing CT apparatus 1 lighter, by making the rotating frame 14 lighter. Because the standing CT apparatus 1 is made lighter, it is possible to have relaxed conditions (e.g., the strength of the floor) for the installation location of the standing CT apparatus 1. For this reason, compared to the comparison example, the standing CT apparatus 1 according to the present embodiment has more options for the installation location.

Further, in the present embodiment, the height h of the outer wall 14b of the rotating frame 14 is described to be equal to or taller than the height of the imaging system. However, the height h of the outer wall 14b is not limited to this example. In another example, the height h of the outer wall 14b of the rotating frame 14 may be shorter than the height of the imaging system.

When the imaging system is attached while hanging from the top face of the rotating frame like in the comparison example, the imaging system will fall when the imaging system comes out of the installation position on the rotating frame. In contrast, in the present embodiment, because the bottom face 14a of the rotating frame 14 is configured to support the imaging system, even if the imaging system comes out of the installation position, it does not necessarily mean that the imaging system will fall. Accordingly, it is sufficient when the height h of the outer wall 14b is tall enough to reduce the chance of the imaging system coming out of the rotating frame 14. By making the height of the outer wall 14b shorter, it is possible to further make the rotating frame 14 lighter in weight.

Second Embodiment

In the first embodiment described above, the outer wall 14b of the rotating frame 14 surrounds the entire outer circumference of the bottom face 14a in a circle. However, it is also acceptable to have the outer wall 14b formed along only a part of the outer circumference of the bottom face 14a.

Figure 4:
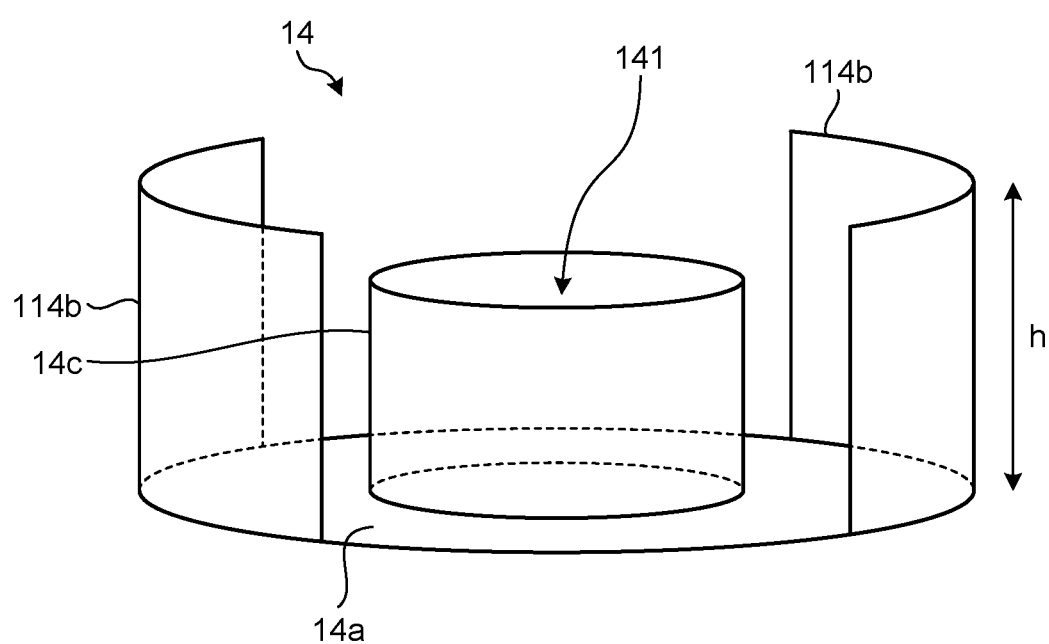
FIG. 4 is a drawing illustrating an example of the appearance of a rotating frame according to a second embodiment.

FIG. 4 is a drawing illustrating an example of the appearance of the rotating frame 14 according to the present embodiment. As illustrated in FIG. 4, an outer wall 114b of the rotating frame 14 according to the present embodiment is provided along a part of the outer circumference of the bottom face 14a.

Due to a centrifugal force generated by the rotation of the rotating frame 14, a load is imposed on the imaging system fixed onto the rotating frame 14. In case that the imaging system has come out of the rotating frame 14 due to the load, the outer wall 114b is provided for the purpose of reducing the chance of the loose imaging system coming out of the rotating frame 14. For this reason, in the present embodiment, the outer wall 114b of the rotating frame 14 is provided at least in a position that, of the outer circumference of the rotating frame 14, corresponds to the installation position of the imaging system. The position corresponding to the installation position of the imaging system denotes the position that, of the outer circumference of the rotating frame 14, corresponds to the outer circumference of a region of the rotating frame 14 in which the imaging system is arranged.

Figure 5:
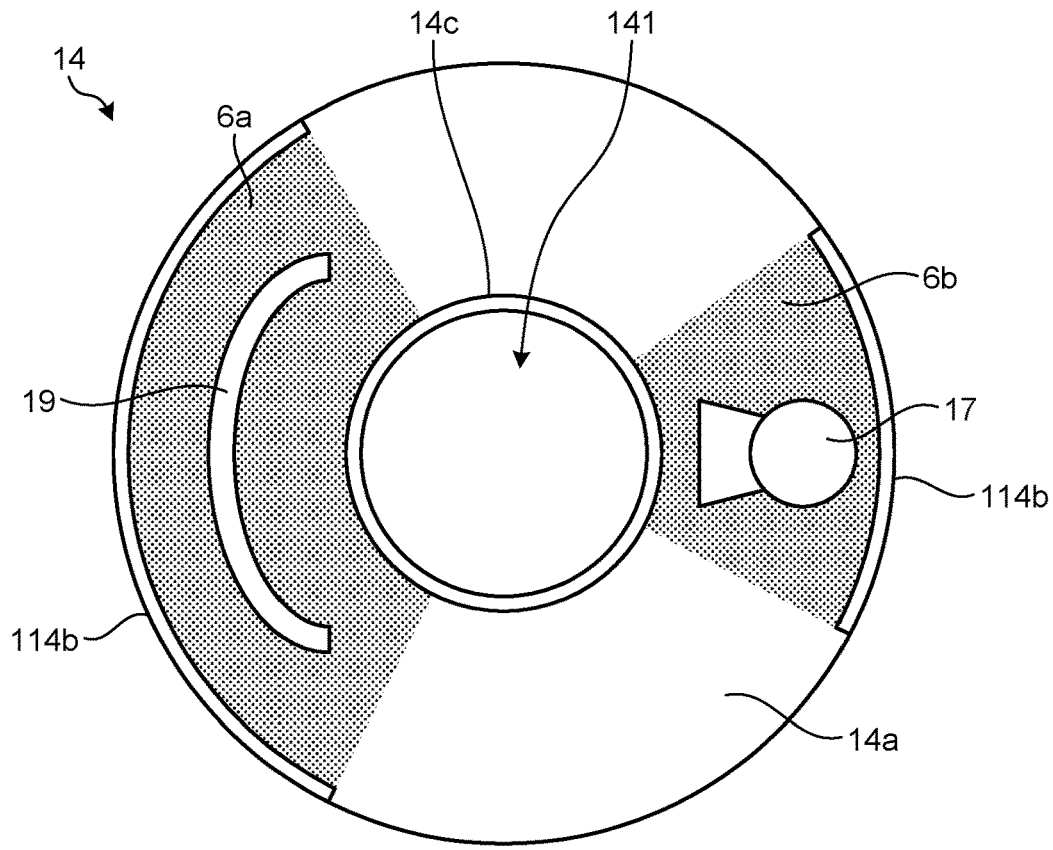
FIG. 5 is an example of a top view of the rotating frame according to the second embodiment.

FIG. 5 is an example of a top view of the rotating frame 14 according to the present embodiment. FIG. 5 illustrates, as the imaging system, the X-ray tube 17 and the X-ray detector 19. On the bottom face 14a of the rotating frame 14, the X-ray tube 17 is installed in a region 6b, whereas the X-ray detector 19 is installed in a region 6a. Each of the regions 6a and 6b has a fan-shaped area defined by two radii of the bottom face 14a and the arcs positioned between the two radii. In the following sections, when not being distinguished from each other, the regions 6a and 6b will be referred to as the regions 6. Further, the quantity of the regions 6 is not limited to two, and it is sufficient when there is at least one region 6.

Of the outer circumference of the rotating frame 14, the outer walls 114b are provided in the ranges corresponding to the arcs of the regions 6. The height of each of the outer walls 114b may be equal to or taller than the height of the imaging system and may be shorter than the height of the imaging system. Further, the rotating frame 14 does not necessarily need to have the inner wall 14c.

FIG. 5 illustrates the X-ray tube 17 and the X-ray detector 19 as the imaging system. However, the outer walls 114b may be provided in positions corresponding to the installation positions of all the constituent elements included in the imaging system, for example. Alternatively, the outer walls 114b may be provided in positions corresponding to the installation positions of certain constituent elements included in the imaging system of which the weight is equal to or heavier than a predetermined level.

Further, in the example in FIG. 5, of the outer circumference of the rotating frame 14, the ranges that do not correspond to the arcs of the regions 6 are not provided with the outer walls 114b. However, possible embodiments are not limited to the configuration in which none of the ranges that do not correspond to the installation positions of the imaging system is provided with the outer wall 114b. It is acceptable to provide one or more of the ranges that do not correspond to the installation positions of the imaging system with the outer wall 114b.

Except for the rotating frame 14, the configuration of the standing CT apparatus 1 according to the present embodiment is the same as that in the first embodiment.

As explained above, in the standing CT apparatus 1 according to the present embodiment, the outer walls 114b of the rotating frame 14 are provided at least in the positions that, of the outer circumference of the rotating frame 14, correspond to the installation positions of the imaging system. Consequently, in the standing CT apparatus 1 according to the present embodiment, it is possible to further make the rotating frame 14 lighter in weight, in addition to the same advantageous effects as those the first embodiment.

Third Embodiment

Figure 6:
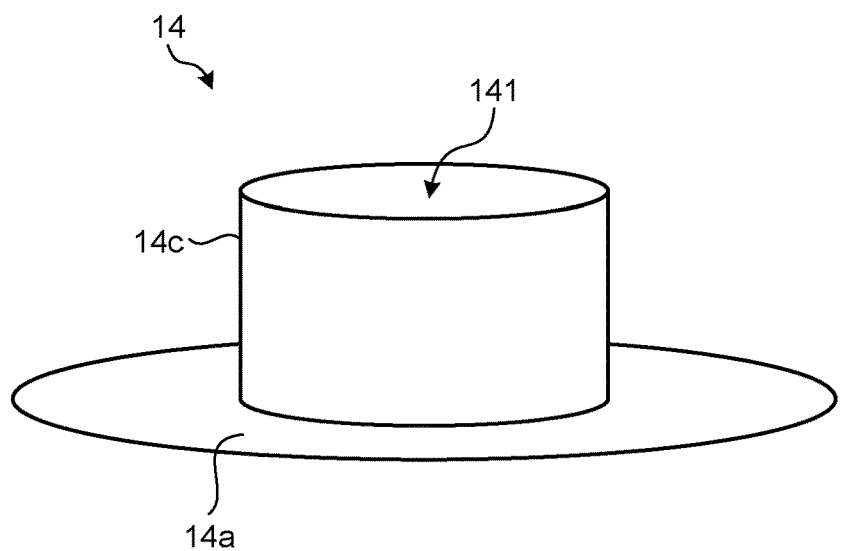
FIG. 6 is a drawing illustrating an example of the appearance of a rotating frame according to a third embodiment.

In a third embodiment, the rotating frame 14 of the standing CT apparatus 1 has no outer wall. FIG. 6 is a drawing illustrating an example of the appearance of the rotating frame according to the present embodiment.

FIG. 6 is a drawing illustrating an example of the appearance of the rotating frame 14 according to the present embodiment. As illustrated in FIG. 6, the rotating frame 14 of the present embodiment has no outer wall provided along the outer circumference. Further, the rotating frame 14 does not need to have the inner wall 14c, either.

Except for the rotating frame 14, the configuration of the standing CT apparatus 1 according to the present embodiment is the same as that in the first embodiment.

As explained above, in the standing CT apparatus 1 according to the present embodiment, the rotating frame 14 has no outer wall provided along the outer circumference. Consequently, in the standing CT apparatus 1 according to the present embodiment, it is possible to further make the rotating frame 14 lighter in weight, in addition to the same advantageous effects as those of the first embodiment.

Fourth Embodiment

In a fourth embodiment, an opening for a maintenance purpose is provided in the gantry cover 12 of the standing CT apparatus 1.

Figure 7:
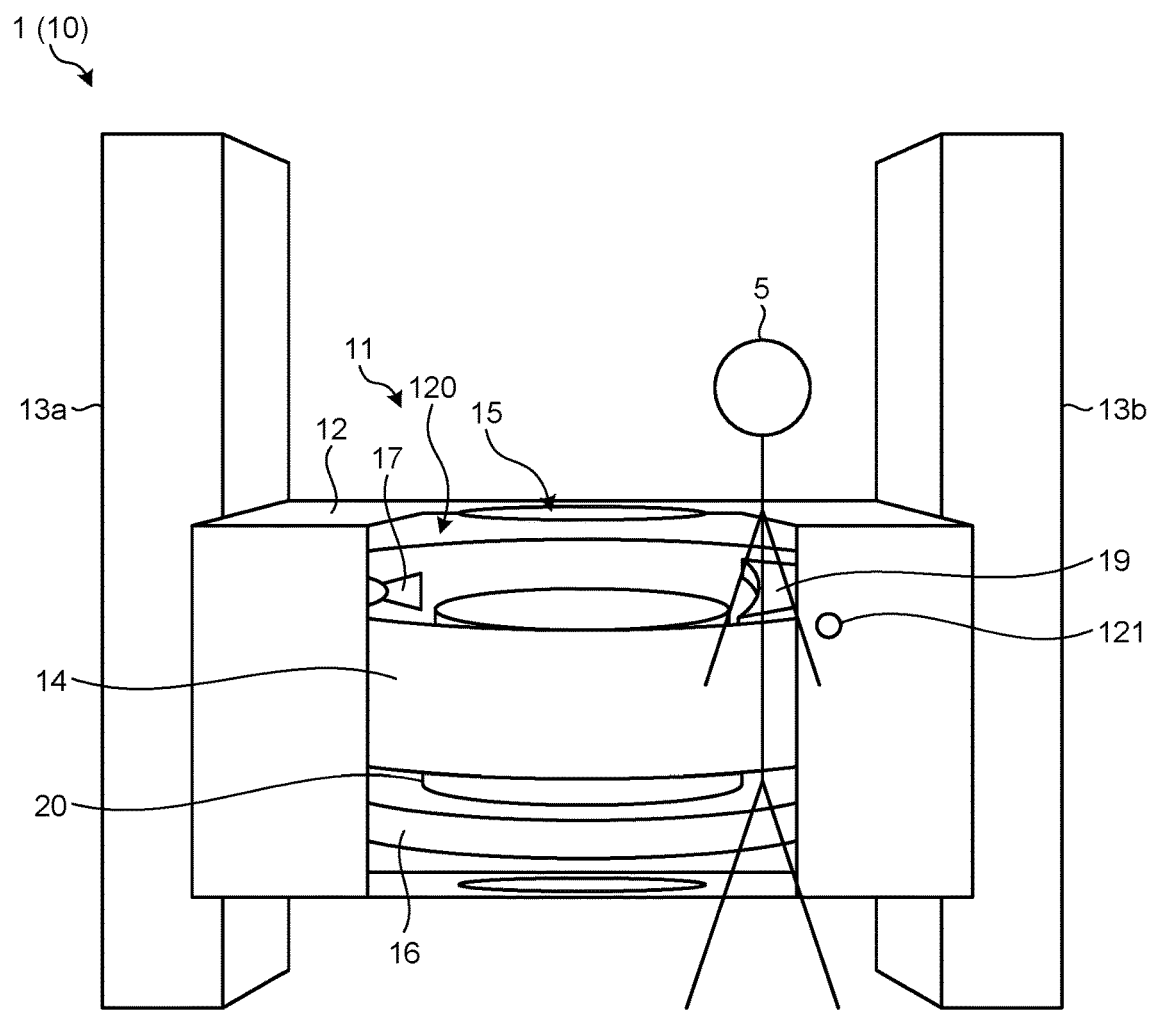
FIG. 7 is a drawing illustrating an example of the appearance of a gantry device included in a standing CT apparatus according to a fourth embodiment.

FIG. 7 is a drawing illustrating an example of the appearance of the gantry device 10 included in the standing CT apparatus 1 according to the present embodiment. As illustrated in FIG. 7, the gantry cover 12 according to the present embodiment is provided with an opening 120.

The opening 120 can be opened and closed, but is closed while the standing CT apparatus 1 is imaging a patient.

Further, for example, the opening 120 is opened when a worker 5 performs maintenance on the gantry 11. The opening and closing configuration of the opening 120 is not particularly limited. For example, the opening and closing may be realized with a sliding door or may be realized with a removable lid.

The opening 120 is provided in one or both of the top face and a lateral face of the gantry cover 12. FIG. 7 illustrates an example in which the opening 120 is provided both in the top face and in a lateral face of the gantry cover 12. The quantity of the opening 120 is not limited to one, and two or more openings 120 may be provided.

Further, in the vicinity of the opening 120, an operation button 121 is provided. The operation button 121 is an operating unit with which the worker 5 is able to electrically input an instruction to rotate the rotating frame 14. For example, when being pressed by the worker 5, the operation button 121 is configured to transmit a signal to the rotation driving device 23 so as to rotate the rotating frame 14. Further, when the worker 5 stops pressing the operation button 121, the transmission of the rotation instructing signal from the operation button 121 to the rotation driving device 23 is also stopped. Only while the signal is received from the operation button 121, i.e., while the operation button 121 is being pressed, the rotation driving device 23 is configured to rotate the rotating frame 14. The worker 5 is an example of the operator.

Upon receipt of the signal from the operation button 121, the rotation driving device 23 is configured to rotate the rotating frame 14 at a speed lower than a rotation speed used at the time of imaging a patient. For example, the rotation driving device 23 may rotate the rotating frame 14 at the speed of approximately one round per minute.

For example, while performing maintenance, the worker 5 causes the rotating frame 14 to rotate by pressing the operation button 121, so as to bring closer the imaging system such as the X-ray tube 17 and the X-ray detector 19 installed in the rotating frame 14. Further, to perform maintenance on the entirety of the rotating frame 14, the worker 5 may cause the rotating frame 14 to rotate every time maintenance work is performed on a certain section, so that the rotating frame 14 rotates one round.

Further, in the present embodiment, the range expressed as "the vicinity of the opening 120" denotes a range within the arm's reach of the worker 5 positioned in front of the opening 120. Further, although FIG. 7 indicates that the operation button 121 is installed on the outside of the gantry cover 12, possible installation positions of the operation button 121 are not limited to this example. For instance, the operation button 121 may be provided on the inside of the gantry cover 12. Further, when the opening 120 is positioned close to the columns 13, the operation button 121 may be provided on one of the columns 13.

The operating unit is not limited to the operation button 121. For example, the operating unit may be a touch panel or the like. Further, the operating unit does not necessarily have to be provided on the gantry device 10 and may be a remote controller or the like that can be carried around by the worker 5.

Except for the gantry cover 12 and the rotation driving device 23, the configuration of the standing CT apparatus 1 according to the present embodiment is the same as that in the first embodiment.

For example, when a rotating frame is attached while hanging frame a supporting frame like in the comparison example described with reference to FIG. 9, because it would be difficult for a worker to perform maintenance on the imaging system from above, it is a common practice at the time of performing maintenance to tilt the entire gantry by 90 degrees, so that the gantry is oriented sideways.

In contrast, in the standing CT apparatus 1 according to the present embodiment, the rotating frame 14 is positioned above the supporting frame 16, while the opening 120 that can be opened and closed is provided in one or both of the top face and a lateral face of the gantry cover 12 that covers the rotating frame 14 and the supporting frame 16. With this configuration, the standing CT apparatus 1 according to the present embodiment makes it easier for the worker 5 to perform the maintenance work and makes it possible for the worker 5 to perform the maintenance work on the imaging system without the need to tilt the entirety of the gantry 11. Consequently, the standing CT apparatus 1 according to the present embodiment does not need to have a configuration to tilt the gantry 11 for the maintenance purposes. It is therefore possible to further make the gantry device 10 lighter in weight, in addition to the same advantageous effects as those of the first embodiment.

Further, the standing CT apparatus 1 according to the present embodiment is provided with the operation button 121 with which the worker 5 is able to electrically input the instruction to rotate the rotating frame 14. With this configuration, the standing CT apparatus 1 according to the present embodiment makes it possible for the worker 5 to easily perform maintenance on the imaging system provided in the rotating frame 14 and on the entire rotating frame 14, through the opening 120. Furthermore, because the worker 5 causes the rotating frame 14 to rotate by using the operation button 121, it is possible to reduce the occurrences of an action of grasping the imaging system provided in the rotating frame 14 to make the rotating frame 14 rotate. It is therefore possible to reduce the load imposed on the imaging system during the maintenance.

Fifth Embodiment

In the fourth embodiment described above, the rotating frame 14 is rotated by the electrical control as a result of the worker 5 pressing the operation button 121; however, possible methods for rotating the rotating frame 14 at the time of performing maintenance are not limited to this example. In the present embodiment, the worker 5 manually causes the rotating frame 14 to rotate, by gripping a grip provided on the rotating frame 14.

Similarly to the fourth embodiment, the gantry cover 12 of the standing CT apparatus 1 according to the present embodiment has the opening 120.

Figure 8:
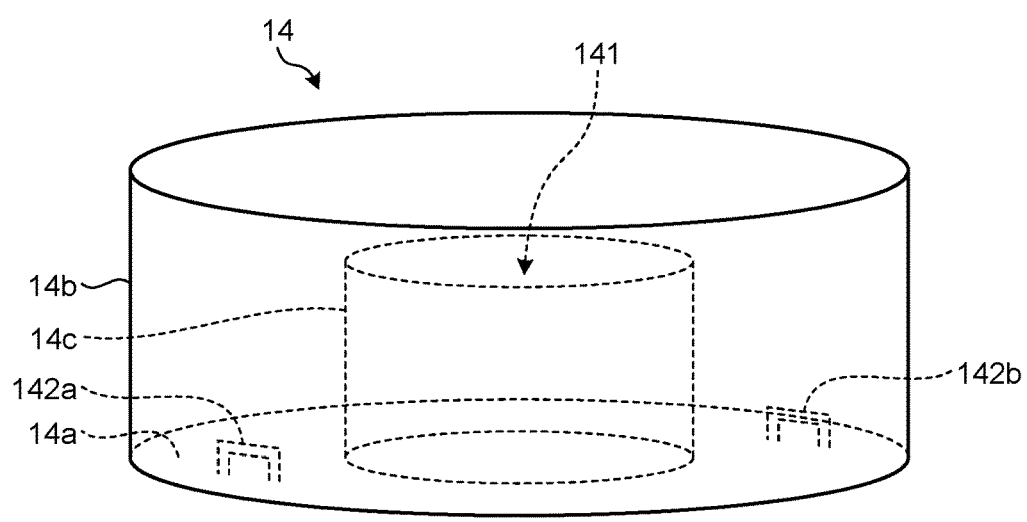
FIG. 8 is a drawing illustrating an example of the appearance of a rotating frame according to a fifth embodiment.

FIG. 8 is a drawing illustrating an example of the appearance of the rotating frame 14 according to the present embodiment. In addition to the configuration in the first embodiment, the rotating frame 14 according to the present embodiment includes grips 142a and 142b. In the following sections, when not being distinguished from each other, the grips 142a and 142b will simply be referred to as the grips 142. For example, the grips 142 are each a handle that can be gripped by the worker 5.

FIG. 8 illustrates an example in which the two grips 142a and 142b are provided on the bottom face 14a of the rotating frame 14. Although the imaging system is omitted from FIG. 8, the grips 142 may be installed in the vicinity of the imaging system, for example.

Further, the quantity of the grips 142 is not limited to this example. It is sufficient when at least one grip 142 is provided. Furthermore, possible installation positions of the grips 142 are not limited to the bottom face 14a. For example, the grips 142 may be provided in the outer wall 14b.

Further, it is sufficient when the grips 142 are present at least at the time of performing maintenance. The grips 142 may be stored or removed in normal times.

For example, the grips 142 may have a tiltable configuration so as to be laid flat in normal times and so as to be raised upright and put in use by the worker 5 as necessary. When this configuration is used, the grips 142 and the rotating frame 14 may be fixed together, for example, by hinges or the like. Further, either the bottom face 14a or the outer wall 14b of the rotating frame 14 may have recess parts capable of storing therein the grips 142 being laid flat.

Further, when the grips 142 are removable, either the bottom face 14a or the outer wall 14b of the rotating frame 14 is provided with connecting parts to which it is possible to attach the grips 142.

In the present embodiment, the standing CT apparatus 1 does not necessarily have to be provided with the operation button 121 with which the worker 5 is able to input an operation to rotate the rotating frame 14, but may be provided with the operation button 121.

As explained above, in the standing CT apparatus 1 according to the present embodiment, because the rotating frame 14 is provided with the grips 142, it is possible to further reduce the occurrences of the action of grasping the imaging system provided in the rotating frame 14 to make the rotating frame 14 rotate, when the worker 5 manually causes the rotating frame 14 to rotate. For this reason, in addition to the same advantageous effects as those of the first embodiment, the standing CT apparatus 1 according to the present embodiment makes it easier for the worker 5 to perform maintenance work and is also able to reduce the load imposed on the imaging system during the maintenance.

In the fourth and the fifth embodiments, the same rotating frame 14 as that in the first embodiment is used as an example; however, it is also acceptable to apply the rotating frame 14 described in the second or the third embodiment to the fourth or the fifth embodiment.

Further, in the first to the fifth embodiments described above, the standing CT apparatus 1 is used as an example of the medical image diagnosis apparatus; however, possible embodiments of the medical image diagnosis apparatus are not limited to this example. For instance, the medical image diagnosis apparatus may be any of various types of modalities such as a standing Magnetic Resonance Imaging (MRI) apparatus, a standing Positron Emission Tomography (PET) apparatus, or a standing Single Photon Emission Computed Tomography (SPECT) apparatus.

According to at least one aspect of the embodiments described above, it is possible to make lighter in weight the medical image diagnosis apparatus capable of imaging the patient in a standing state or a sitting state.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus, comprising:
    a first supporting part configured to support an imaging system related to imaging a subject to be examined;
    a second supporting part configured to support the first supporting part from underneath the first supporting part; and
    at least one column configured to support the second supporting part so that the second supporting part is movable along a vertical direction,
    wherein the first supporting part includes
        a bottom face configured to entirely support the imaging system, and
        a lateral wall provided along an outer circumference of the first supporting part, without supporting the imaging system.

2. The medical image diagnosis apparatus according to claim 1, wherein
    the imaging system includes an X-ray tube and an X-ray detector configured to detect X-rays,
    the first supporting part is a rotating frame configured to support at least the X-ray tube and the X-ray detector, and
    the second supporting part is a supporting frame configured to rotatably support the rotating frame.

3. The medical image diagnosis apparatus according to claim 1, wherein a height of the lateral wall of the first supporting part is equal to or taller than a height of the imaging system.

4. The medical image diagnosis apparatus according to claim 1, wherein a height of the lateral wall of the first supporting part is shorter than a height of the imaging system.

5. The medical image diagnosis apparatus according to claim 1, wherein the lateral wall of the first supporting part is provided at least in a position that, of the outer circumference of the first supporting part, corresponds to an installation position of the imaging system.

6. The medical image diagnosis apparatus according to claim 1, further comprising:
    a cover configured to cover the first supporting part and the second supporting part, wherein
    an opening that can be opened and closed is provided in one or both of a top face and a lateral face of the cover.

7. The medical image diagnosis apparatus according to claim 6, wherein, in a vicinity of the opening, an operation unit is provided, with which an operator is able to electrically input an instruction to rotate the first supporting part.

8. The medical image diagnosis apparatus according to claim 6, wherein the first supporting part includes a grip.

* * * * *